(12) United States Patent
Nishimura

(10) Patent No.: US 8,323,657 B2
(45) Date of Patent: Dec. 4, 2012

(54) ANTIGENIC POLYPEPTIDE USABLE AS THERAPEUTIC AGENT FOR MALIGNANT NEOPLASM

(75) Inventor: Takashi Nishimura, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 193 days.

(21) Appl. No.: 12/312,232

(22) PCT Filed: Oct. 2, 2007

(86) PCT No.: PCT/JP2007/001073
§ 371 (c)(1),
(2), (4) Date: Jun. 12, 2009

(87) PCT Pub. No.: WO2008/053579
PCT Pub. Date: May 8, 2008

(65) Prior Publication Data
US 2010/0034841 A1 Feb. 11, 2010

(30) Foreign Application Priority Data

Oct. 30, 2006 (JP) .................................. 2006-294763

(51) Int. Cl.
C07K 5/00 (2006.01)
(52) U.S. Cl. .................... 424/185.1; 514/19.2; 530/328; 530/327; 530/326; 530/325; 530/324; 530/350
(58) Field of Classification Search .......................... None
See application file for complete search history.

(56) References Cited

U.S. PATENT DOCUMENTS

| | | | |
|---|---|---|---|
| 5,342,774 A | 8/1994 | Boon et al. | |
| 5,591,430 A | 1/1997 | Townsend et al. | |
| 5,750,395 A * | 5/1998 | Fikes et al. ..................... | 435/325 |
| 5,965,535 A | 10/1999 | Chaux et al. | |
| 7,311,914 B2 * | 12/2007 | Zhang et al. ............... | 424/184.1 |
| 7,547,439 B1 * | 6/2009 | Huang et al. ............... | 424/184.1 |

FOREIGN PATENT DOCUMENTS

| | | |
|---|---|---|
| JP | 2004-123752 | 4/2004 |
| WO | WO 92/20356 | 11/1992 |
| WO | WO 95/19783 | 7/1995 |
| WO | WO 97/11669 | 4/1997 |
| WO | WO 2000/20581 | 4/2000 |
| WO | WO 00/52045 | 9/2000 |
| WO | WO 00/78806 | 12/2000 |
| WO | 02/095051 | * 11/2002 |
| WO | WO 02/095051 | 11/2002 |
| WO | WO 2006/091734 A | 8/2006 |

OTHER PUBLICATIONS

Essell (J. NIH Res. 1995 7:46).*
Spitler (Cancer Biotherapy, 1995, 10:1-3).*
Boon (Adv. Can. Res. 1992 58:177-210).*
Pascal Chaux et al., "A MAGE-1 Peptide Recognized on HLA-DR15 by CD4+ Cells", Eur. J. Immunol, 2001, pp. 1910-1916, vol. 31.
Yi Zhang et al., "A MAGE-3 Peptide Presented by HLA-DR1 to CD4+ T cells that were isolated from . . . ", Journal of Immunology, 2003, pp. 219-225, vol. 171, No. 1.
Cluseppe Consogno et al., "Identification of Immunodominant Regions Among Promiscuous HLA-DR-Restricted CD4+ T-cell . . . ", 2003, pp. 1038-1044, vol. 101, No. 3.
Xiao-Fei Wang et al., "Selective Identification of HLA-DP4 Binding T Cell Epitopes Encoded by the MAGE-A Gene Family", Sep. 20, 2006, pp. 287-290, vol. 56.
Yasuhisa Imai et al., "Sequence Analysis of the MAGE Gene Family Encoding Human Tumor-Rejection Antigens", 1995, pp. 287-290, vol. 160.
Morten Nielsen et al., "Improved Predition of MHC Class 1 and Class 2 Epitopes Using a Novel Gibbs Sampling . . . ", Bioinformatics, 2004, pp. 1388-1397, vol. 20, No. 9.
Guang Lan Zhang et al., "Multipred: A Computational System for Predition of Promiscuous HLA Binding Peptides", Nucleic Acids Research, 2005, vol. 33, W172-W179.
Harpreet Singh et al., "ProPred: Prediction of HLA-DR Binding Sites", Bioinformatics, 2001, pp. 1236-1237, vol. 17.
Yue Zhang et al., "The Cellular and Molecular Mechanism Underlying Th1 Cell Adjuvant Therapy . . . ", 10th Fundamental Cancer Immunology Meeting Brief, Jun. 30, 2006, p. 43.
Suzanne L. Topalian et al., "Human CD4+ T Cells Specifically Recognize a Shared Melanoma-Associated Antigen . . . ", Proc. Natl. Acad. Sci. USA, 1994, pp. 9461-9465, vol. 91.
Etienne De Plaen et al., "Structure, Chromosomal Localization, and Expression of 12 Genes of the MAGE Family", Immunogenetics, 1994, pp. 360-369, vol. 40.
Cetia Traversari et al., "Transfection and Expression of a Gene Coding for a Human Melanoma Antigen . . . ", Immunogenetics, 1992, pp. 145-152, vol. 35.
P. Van Der Bruggen et al., "A Gene Encoding an Antigen Recognized by Cytolytic T Lymphocytes on a Human Melanoma", Science, Dec. 13, 1991, pp. 1643-1647, vol. 35.
Maie-Theresse Duffour et al., "A MAGE-A4 Peptide Presented by HLA-A2 is Recognized by Cytolytic T Lymphocytes", Eur. J. Immunol, 1999, pp. 3329-3337, vol. 20.
Yoshihiro Miyahara, "Determination of Cellularly Processed HLA-A2402-Restricted Novel CTL Epitopes . . . ", Clin Cancers Res., Aug. 1, 2005, pp. 5581-5589, vol. 121.
XP002548510 "Human MAGE-A4 Polypeptide" in Database Geneseq of Jul. 15, 2004 re the US Patent Publication No. 2004/0033541 A of Zhang et al.
XP002548511 "Human MAGE-3 Segment 18" in Database Geneseq of May 8, 2002 re the PCT Application International Publication No. WO 01/90197 A of Australian National Univ.
XP002548512 "MAGE-A4 Antigenic Peptide Epitope (residues 264-279)" in Database Geneseq of Aug. 10, 2000 re the PCT Application International Publication No. WO 00/20445 of Chaux.
XP002630781 "Identification of novel helper epitopes . . . " by T. Ohkuri et al. in British Journal of Cancer, vol. 100, No. 7, Mar. 2009, pp. 1135-1143.
XP002630783 "MAGE-A3 and MAGE-A4 specific CD4+ T cells . . . " by Valerie Cesson et al. in Cancer Immunology Immunotherapy, vol. 60, No. 1, Jan. 2011, pp. 23-35.

* cited by examiner

Primary Examiner — Sheela J Huff
(74) Attorney, Agent, or Firm — DLA Piper LLP (US)

(57) ABSTRACT

This invention provides a new tumor antigen having an epitope that induces a Th1 cell (a CD4-positive T cell specific to MAGE-A4), and a method ot application thereof.

9 Claims, 9 Drawing Sheets

SEQUENCE LISTING

```
<160> NUMBER OF SEQ ID NOS: 32

<210> SEQ ID NO 1
<211> LENGTH: 20
<212> TYPE: PRT
<213> ORGANISM: Homo sapiens

<400> SEQUENCE: 1

Tyr Arg Gln Val Pro Gly Ser Asn Pro Ala Arg Tyr Glu Phe Leu Trp
1               5                   10                  15

Gly Pro Arg Ala
            20

<210> SEQ ID NO 2
<211> LENGTH: 20
<212> TYPE: PRT
<213> ORGANISM: Homo sapiens

<400> SEQUENCE: 2

Ala Glu Thr Ser Tyr Val Lys Val Leu Glu His Val Val Arg Val Asn
1               5                   10                  15

Ala Arg Val Arg
            20

<210> SEQ ID NO 3
<211> LENGTH: 317
<212> TYPE: PRT
<213> ORGANISM: Homo sapiens

<400> SEQUENCE: 3

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
        115                 120                 125

Glu Leu Val Thr Lys Ala Glu Met Leu Glu Arg Val Ile Lys Asn Tyr
    130                 135                 140

Lys Arg Cys Phe Pro Val Ile Phe Gly Lys Ala Ser Glu Ser Leu Lys
```

```
                145                 150                 155                 160
Met Ile Phe Gly Ile Asp Val Lys Glu Val Asp Pro Thr Ser Asn Thr
                    165                 170                 175

Tyr Thr Leu Val Thr Cys Leu Gly Leu Ser Tyr Asp Gly Leu Leu Gly
                180                 185                 190

Asn Asn Gln Ile Phe Pro Lys Thr Gly Leu Leu Ile Ile Val Leu Gly
            195                 200                 205

Thr Ile Ala Met Glu Gly Asp Ser Ala Ser Glu Glu Ile Trp Glu
        210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Asn Tyr
                245                 250                 255

Leu Glu Tyr Arg Gln Val Pro Gly Ser Asn Pro Ala Arg Tyr Glu Phe
                260                 265                 270

Leu Trp Gly Pro Arg Ala Leu Ala Glu Thr Ser Tyr Val Lys Val Leu
                275                 280                 285

Glu His Val Val Arg Val Asn Ala Arg Val Ile Ala Tyr Pro Ser
        290                 295                 300

Leu Arg Gln Ala Ala Leu Leu Glu Glu Glu Gly Val
305                 310                 315

<210> SEQ ID NO 4
<211> LENGTH: 954
<212> TYPE: DNA
<213> ORGANISM: Homo sapiens

<400> SEQUENCE: 4
atgtcttctg agcagaagag tcagcactgc aagcctgagg aaggcgttga ggcccaagaa      60
gaggccctgg gcctggtggg tgcgcaggct cctactactg aggagcagga ggctgctgtc     120
tcctcctcct ctcctctggt ccctggcacc ctggaggaag tgcctgctgc tgagtcagca     180
ggtcctcccc agagtcctca gggagcctct gccttaccca ctaccatcag cttcacttgc     240
tggaggcaac ccaatgaggg ttccagcagc caagaagagg aggggccaag cacctcgcct     300
gacgcagagt ccttgttccg agaagcactc agtaacaagg tggatgagtt ggctcatttt     360
ctgctccgca gtatcgagc caaggagctg gtcacaaagg cagaaatgct ggagagagtc     420
atcaaaaatt acaagcgctg ctttcctgtg atcttcggca agcctccga gtccctgaag     480 atgatctttg gcattgacgt gaaggaagtg gaccccacca gcaacaccta cacccttgtc     540
acctgcctgg gcctttccta tgatggcctg ctgggtaata atcagatctt tcccaagaca     600
ggccttctga taatcgtcct gggcacaatt gcaatggagg gcgacagcgc tctgaggag     660 gaaatctggg aggagctggg tgtgatgggg gtgtatgatg ggagggagca cactgtctat     720
ggggagccca gaaaactgct cacccaagat tgggtgcagg aaaactacct ggagtaccgg     780
caggtacccg gcagtaatcc tgcgcgctat gagttcctgt ggggtccaag ggctctggct     840
gaaaccagct atgtgaaagt cctggagcat gtggtcaggg tcaatgcaag agttcgcatt     900
gcctacccat ccctgcgtca gcagctttg ttagaggagg aagagggagt ctga           954

<210> SEQ ID NO 5
<211> LENGTH: 26
<212> TYPE: DNA
<213> ORGANISM: Artificial sequence
<220> FEATURE:
<223> OTHER INFORMATION: primer
```

<400> SEQUENCE: 5
ggatccatgt cttctgagca gaagag                                   26

<210> SEQ ID NO 6
<211> LENGTH: 30
<212> TYPE: DNA
<213> ORGANISM: Artificial sequence
<220> FEATURE:
<223> OTHER INFORMATION: primer

<400> SEQUENCE: 6
aagctttcag actccctctt cctcctctaa                               30

<210> SEQ ID NO 7
<211> LENGTH: 11
<212> TYPE: PRT
<213> ORGANISM: Homo sapiens

<400> SEQUENCE: 7

Ala Glu Thr Ser Tyr Val Lys Val Leu Glu His
1               5                   10

<210> SEQ ID NO 8
<211> LENGTH: 12
<212> TYPE: PRT
<213> ORGANISM: Homo sapiens

<400> SEQUENCE: 8

Ala Glu Thr Ser Tyr Val Lys Val Leu Glu His Val
1               5                   10

<210> SEQ ID NO 9
<211> LENGTH: 13
<212> TYPE: PRT
<213> ORGANISM: Homo sapiens

<400> SEQUENCE: 9

Ala Glu Thr Ser Tyr Val Lys Val Leu Glu His Val Val
1               5                   10

<210> SEQ ID NO 10
<211> LENGTH: 14
<212> TYPE: PRT
<213> ORGANISM: Homo sapiens

<400> SEQUENCE: 10

Ala Glu Thr Ser Tyr Val Lys Val Leu Glu His Val Val Arg
1               5                   10

<210> SEQ ID NO 11
<211> LENGTH: 15
<212> TYPE: PRT
<213> ORGANISM: Homo sapiens

<400> SEQUENCE: 11

Ala Glu Thr Ser Tyr Val Lys Val Leu Glu His Val Val Arg Val
1               5                   10                  15

<210> SEQ ID NO 12
<211> LENGTH: 15
<212> TYPE: PRT
<213> ORGANISM: Homo sapiens

<400> SEQUENCE: 12

Glu Thr Ser Tyr Val Lys Val Leu Glu His Val Val Arg Val Asn

```
                     1               5                  10                 15
```

```
<210> SEQ ID NO 13
<211> LENGTH: 15
<212> TYPE: PRT
<213> ORGANISM: Homo sapiens

<400> SEQUENCE: 13

Thr Ser Tyr Val Lys Val Leu Glu His Val Val Arg Val Asn Ala
1               5                   10                  15

<210> SEQ ID NO 14
<211> LENGTH: 15
<212> TYPE: PRT
<213> ORGANISM: Homo sapiens

<400> SEQUENCE: 14

Ser Tyr Val Lys Val Leu Glu His Val Val Arg Val Asn Ala Arg
1               5                   10                  15

<210> SEQ ID NO 15
<211> LENGTH: 15
<212> TYPE: PRT
<213> ORGANISM: Homo sapiens

<400> SEQUENCE: 15

Tyr Val Lys Val Leu Glu His Val Val Arg Val Asn Ala Arg Val
1               5                   10                  15

<210> SEQ ID NO 16
<211> LENGTH: 15
<212> TYPE: PRT
<213> ORGANISM: Homo sapiens

<400> SEQUENCE: 16

Val Lys Val Leu Glu His Val Val Arg Val Asn Ala Arg Val Arg
1               5                   10                  15

<210> SEQ ID NO 17
<211> LENGTH: 14
<212> TYPE: PRT
<213> ORGANISM: Homo sapiens

<400> SEQUENCE: 17

Lys Val Leu Glu His Val Val Arg Val Asn Ala Arg Val Arg
1               5                   10

<210> SEQ ID NO 18
<211> LENGTH: 13
<212> TYPE: PRT
<213> ORGANISM: Homo sapiens

<400> SEQUENCE: 18

Val Leu Glu His Val Val Arg Val Asn Ala Arg Val Arg
1               5                   10

<210> SEQ ID NO 19
<211> LENGTH: 20
<212> TYPE: PRT
<213> ORGANISM: Homo sapiens

<400> SEQUENCE: 19

Ala Glu Thr Ser Tyr Ala Lys Val Leu Glu His Val Val Arg Val Asn
1               5                   10                  15

Ala Arg Val Arg
```

```
<210> SEQ ID NO 20
<211> LENGTH: 20
<212> TYPE: PRT
<213> ORGANISM: Homo sapiens

<400> SEQUENCE: 20

Ala Glu Thr Ser Tyr Val Ala Val Leu Glu His Val Val Arg Val Asn
1               5                   10                  15

Ala Arg Val Arg
            20

<210> SEQ ID NO 21
<211> LENGTH: 20
<212> TYPE: PRT
<213> ORGANISM: Homo sapiens

<400> SEQUENCE: 21

Ala Glu Thr Ser Tyr Val Lys Ala Leu Glu His Val Val Arg Val Asn
1               5                   10                  15

Ala Arg Val Arg
            20

<210> SEQ ID NO 22
<211> LENGTH: 20
<212> TYPE: PRT
<213> ORGANISM: Homo sapiens

<400> SEQUENCE: 22

Ala Glu Thr Ser Tyr Val Lys Val Ala Glu His Val Val Arg Val Asn
1               5                   10                  15

Ala Arg Val Arg
            20

<210> SEQ ID NO 23
<211> LENGTH: 20
<212> TYPE: PRT
<213> ORGANISM: Homo sapiens

<400> SEQUENCE: 23

Ala Glu Thr Ser Tyr Val Lys Val Leu Ala His Val Val Arg Val Asn
1               5                   10                  15

Ala Arg Val Arg
            20

<210> SEQ ID NO 24
<211> LENGTH: 20
<212> TYPE: PRT
<213> ORGANISM: Homo sapiens

<400> SEQUENCE: 24

Ala Glu Thr Ser Tyr Val Lys Val Leu Glu Ala Val Val Arg Val Asn
1               5                   10                  15

Ala Arg Val Arg
            20

<210> SEQ ID NO 25
<211> LENGTH: 20
<212> TYPE: PRT
<213> ORGANISM: Homo sapiens

<400> SEQUENCE: 25
```

```
Ala Glu Thr Ser Tyr Val Lys Val Leu Glu His Ala Val Arg Val Asn
1               5                   10                  15

Ala Arg Val Arg
            20

<210> SEQ ID NO 26
<211> LENGTH: 20
<212> TYPE: PRT
<213> ORGANISM: Homo sapiens

<400> SEQUENCE: 26

Ala Glu Thr Ser Tyr Val Lys Val Leu Glu His Val Ala Arg Val Asn
1               5                   10                  15

Ala Arg Val Arg
            20

<210> SEQ ID NO 27
<211> LENGTH: 20
<212> TYPE: PRT
<213> ORGANISM: Homo sapiens

<400> SEQUENCE: 27

Ala Glu Thr Ser Tyr Val Lys Val Leu Glu His Val Val Ala Val Asn
1               5                   10                  15

Ala Arg Val Arg
            20

<210> SEQ ID NO 28
<211> LENGTH: 20
<212> TYPE: PRT
<213> ORGANISM: Homo sapiens

<400> SEQUENCE: 28

Ala Glu Thr Ser Tyr Val Lys Val Leu Glu His Val Val Arg Ala Asn
1               5                   10                  15

Ala Arg Val Arg
            20

<210> SEQ ID NO 29
<211> LENGTH: 20
<212> TYPE: PRT
<213> ORGANISM: Homo sapiens

<400> SEQUENCE: 29

Ala Glu Thr Ser Tyr Val Lys Val Leu Glu His Val Val Arg Val Ala
1               5                   10                  15

Ala Arg Val Arg
            20

<210> SEQ ID NO 30
<211> LENGTH: 20
<212> TYPE: PRT
<213> ORGANISM: Homo sapiens

<400> SEQUENCE: 30

Ala Glu Thr Ser Tyr Val Lys Val Leu Glu His Val Val Arg Val Asn
1               5                   10                  15

Gly Arg Val Arg
            20

<210> SEQ ID NO 31
<211> LENGTH: 20
<212> TYPE: PRT
```

```
<213> ORGANISM: Homo sapiens

<400> SEQUENCE: 31

Ala Glu Thr Ser Tyr Val Lys Val Leu Glu His Val Val Arg Val Asn
1               5                   10                  15

Ala Ala Val Arg
            20

<210> SEQ ID NO 32
<211> LENGTH: 40
<212> TYPE: PRT
<213> ORGANISM: Homo sapiens

<400> SEQUENCE: 32

Asn Tyr Lys Arg Cys Phe Pro Val Ile Phe Gly Lys Gly Gly Gly Gly
1               5                   10                  15

Gly Gly Ala Leu Ala Glu Thr Ser Tyr Val Lys Val Leu Glu His Val
            20                  25                  30

Val Arg Val Asn Ala Arg Val Arg
            35                  40
```

ANTIGENIC POLYPEPTIDE USABLE AS THERAPEUTIC AGENT FOR MALIGNANT NEOPLASM

TECHNICAL FIELD

The present invention relates to an antigenic polypeptide useful for cancer immunotherapy and a treating agent for malignant neoplasm containing the antigenic polypeptide.

BACKGROUND OF THE ART

One of intractable cancer (malignant neoplasm) treatment techniques is immunotherapy that causes regression of a cancer cell by boosting the immune system in an individual patient. The important point is to find a method for encouraging the immune system to recognize a cancer cell as foreign matter and inducing an immunocyte having aggressiveness against the cancer cell.

Key immunocytes associated with antitumor immunity include a cytotoxic T cell expressing a CD8 cell surface protein (CD8-positive T cell) and a T cell expressing a CD4 cell surface protein (CD4-positive T cell). The CD8-positive T cell, when activated, lyses a cell that presents an antigen binding to an HLA Class 1 molecule. The CD4-positive T cell is a cytokine-secreting Th cell that provides the CD8-positive T with a helper function, i.e. cell induction and preservation, when it is activated by a macrophage and/or a dendritic cell presenting an antigen by an HLA Class II molecule. Conventionally, Th cells are classified into Th1 cell (producing INF-γ, etc.), Th2 cell (producing IL-4, etc.) and Th0 cell (known as low cytokine producing ability or producing both INF-γ and IL-4, etc.), and respective roles thereof are being specifically provided. The CD4-positive T cell can be provided with effector functions by its indirect mechanism against an MHC Class II molecule negative tumor (MHC Class II-tumor), e.g., via activation of a macrophage, or direct mechanism against an MHC Class II positive tumor (MHC Class II-positive tumor).

Conventional T cell researches in human cancer immunotherapy focus on identification and induction of CD8-positive HLA Class I restricted CTL response (Patent Document 1). With regard to CD4-positive T cell, a report on the identification of a tyrosinase cancer antigen and its epitope corresponding to a CD4-positive T cell is given (Patent Document 2). Tyrosinase is known as the only antigen specific to melanoma associative tissues, which binds to an MHC Class II molecule expressed in normal cells and tumor cells of melanocyte line and presented as a specific target of a CD4-positive melanoma-reactive T cell (Non-Patent Document 1). However, due to its expression only in limited types of tumor, the tyrosinase antigen cannot be assuredly defined as a promising cancer antigen in cancer immunotherapy.

A recent report presents a gene family encoding a tumor-specific antigen that is recognized by a CD8-positive T cell (MAGE) (Non-Patent Documents 2 to 4, and Patent Documents 3 and 4). This MAGE gene family consists of about 12 members expressed in various types of tumor. According to a study on an MAGE-A3 thereof, the MAGE-A3 is a peptide whose partial peptide fragment is presented by an HLA Class I molecule (Patent Document 5) and another partial peptide fragment binds to an HLA Class II molecule (Patent Documents 6 and 7).

Although it was found that the MAGE-A3 includes an HLA Class II-binding peptide, many individual patients express no appropriate HLA molecule, resulting in unsuccessful therapies, such as activation of a helper T cell by the MAGE-A3 peptide. Therefore, identification of more tumor-associated antigens, which bind to an MHC Class II molecule and include an epitope recognized by a CD4-positive T cell, is significantly required.

As another MAGE family, MAGE-A4 is a tumor-specific antigen whose all 317 constituents are amino acid residues (SEQ ID No: 3). MAGE-A4 is highly expressed in many tumor-histologic cases such as melanoma, esophageal cancer, head and neck cancer and lung cancer, but such expression is not observed in normal cells other than testis and placenta (Non-Patent Document 5).

With regard to MAGE-A4 antigenicity, it is reported that MAGE-A4 amino acid sequence of No. 143 to 151 presents an epitope recognized by a CD8-positive T cell (Non-Patent Document 6). Also, MAGE-A4's affinity to gankyrin is described (Patent Document 8), and more specifically, a portion thereof corresponding to amino acids of No. 211 to 317 at C terminus of MAGE-A4 is associated with the affinity to gankyrin. Meanwhile, it is also reported that a C terminus portion, containing 97 amino acid residues from No. 211 amino acid of MAGE-A4, has no ability to bind to gankyrin.
Non-Patent Document 1: Topalian, S. L. et al., Proc. Natl. Acad. Sci. USA, Vol. 91, pp. 9461-9465, 1994
Non-Patent Document 2: Plaen et al., Immunogenetics, Vol. 40, pp. 360-369, 1994
Non-Patent Document 3: Traversari et al., Immunogenetics, Vol. 35, p 145, 1992
Non-Patent Document 4: van der Bruggen et al., Science, Vol. 254, p 1643, 1991
Non-Patent Document 5: Duffour M. T. et al., Eur. J. Immunol., Vol 29, pp. 3329-3337, 1999
Non-Patent Document 6: Yoshihiro M. et al., Clin. Cancer Res., Vol 121, pp. 5581-5589, 2005
Patent Document 1: WO 95/19783
Patent Document 2: WO 97/11669
Patent Document 3: PCT/US 92/04,354
Patent Document 4: U.S. Pat. No. 5,342,774
Patent Document 5: U.S. Pat. No. 5,591,430
Patent Document 6: U.S. Pat. No. 5,965,535
Patent Document 7: PCT/US 99/21,230
Patent Document 8: Japanese Unexamined Patent Application Publication No. 2004-123752

DISCLOSURE OF THE INVENTION

Problem to be Solved

The present invention provides a new treating agent useful in treating malignant neoplasm using a tumor antigen, and a tumor antigen useful as the treating agent.

The inventors experimentally found that a treating agent containing a tumor antigen and a Th cell specific to the tumor antigen has an effect of significantly regressing malignant neoplasm expressing the tumor antigen and also specified a new antigenic peptide useful as the tumor antigen and completed each of the following inventions.

(1) A polypeptide which comprises an amino acid sequence having the following characteristic a), b), c), d), e) or f) and has a cytokine-producing activity in a Th cell specific to MAGE-A4:
  a) An amino acid sequence represented by SEQ ID No: 1 or No: 2;
  b) An amino acid sequence, wherein one to several tens of any amino acids are added to N terminus and/or C terminus of an amino acid sequence represented by SEQ ID No: 1 or No: 2;

c) An amino acid sequence, wherein one to five amino acids from N terminus and/or C terminus of an amino acid sequence represented by SEQ ID No: 1 or No: 2 are deleted;
d) An amino acid sequence, wherein one to several amino acid residues of an amino acid sequence represented by SEQ ID No: 1 or No: 2 are substituted and/or deleted;
e) An amino acid sequence, wherein one to several tens of any amino acids are added to N terminus and/or C terminus of an amino acid sequence, wherein one to several amino acid residues of an amino acid sequence represented by SEQ ID No: 1 or No: 2 are substituted and/or deleted; and
f) An amino acid sequence, wherein one to several amino acid residues are substituted in an amino acid sequence, wherein one to five amino acids from N terminus and/or C terminus of an amino acid sequence represented by SEQ ID No: 1 or No: 2 are deleted.

(2) The polypeptide according to item (1), wherein a polypeptide comprising an amino acid sequence having the above characteristic b), c), d), e) or f) comprises an epitope of a polypeptide comprising an amino acid sequence represented by SEQ ID No: 1 or No: 2, the epitope inducing a Th cell specific to MAGE-A4 from a CD4-positive T cell.

(3) A nucleic acid encoding the polypeptide according to item (1) or (2).

(4) A vector containing the nucleic acid according to item (3).

(5) An antibody that specifically binds to the polypeptide according to item (1) or (2).

(6) A vaccine for immunotherapy for malignant neoplasm containing at least one type of the polypeptides according to item (1) or (2) as an active ingredient.

(7) A method for inducing a Th cell specific to MAGE-A4 comprising a process for incubating in vitro at least one type of the polypeptides according to item (1) or (2), an antigen-presenting cell and a CD4-positive T cell.

(8) A treating agent for malignant neoplasm containing the polypeptides according to item (1) or (2) and a Th cell specific to the polypeptide or MAGE-A4.

Advantageous Effect of the Invention

A peptide of this invention induces a Th cell specific to MAGE-A4 (hereinafter called A4/Th cell) by incubating the peptide, an antigen-presenting cell and a CD4-positive T cell, having a cytokine-producing activity in the A4/Th cell. Due to an ability of the A4/Th cell to specifically attack malignant neoplasm expressing MAGE-A4, the peptide of this invention can be used as an ingredient of a treating agent for malignant neoplasm. The polypeptide of this invention, having a small number of constituent amino acid residues, can be produced in large quantity not only by gene recombination method but also organic synthetic method. Therefore, the polypeptide of this invention can be supplied in clinical studies and applications in a stable and least expensive manner.

A treating agent containing a polypeptide of this invention, comprising a tumor antigen and a Th cell specific to the tumor antigen combined, can actively promote the production of cytokines in the Th cell. Cytokines produced induce in vivo antitumor immune response specific to malignant neoplasm expressing the tumor antigen to regress tumor.

BRIEF DESCRIPTION OF THE DRAWINGS

The above and other objects of the invention will be seen by reference to the description taken in connection with the drawings, in which.

BEST MODE FOR CARRYING OUT THE INVENTION

Figure 1:
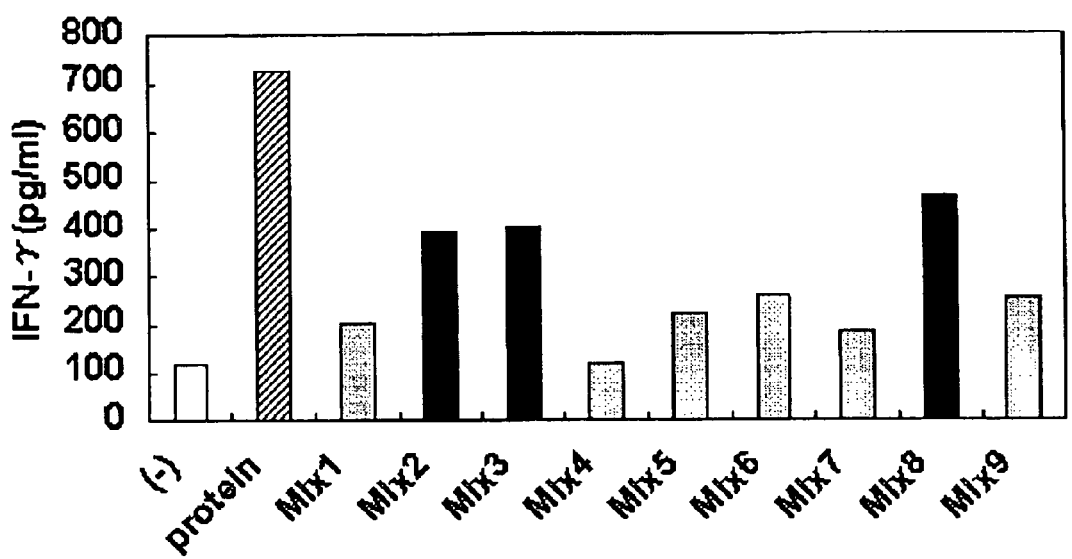
FIG. 1 is a graph indicative of volumes of INF-γ produced by an A4/Th cell induced from a human whose HLA genotype is HLA-DRB1 by adding mixed peptides MIX1 to MIX9 to the A4/Th cell, respectively.

The present invention relates to a tumor antigen as a partial polypeptide of MAGE-A4, and a treating agent for malignant neoplasm containing the tumor antigen and a Th cell specific to the tumor antigen. A treating agent for malignant neoplasm of this invention preferably comprises a tumor antigen as a partial polypeptide of MAGE-A4, and a Th cell specific to the tumor antigen induced by the tumor antigen from a CD4-positive T cell collected from a patient to be treated.

A treating agent for malignant neoplasm of this invention has a significant effect of regressing malignant neoplasm by comprising a tumor antigen as a partial polypeptide of MAGE-A4 and a Th cell specific to the tumor antigen combined, compared with a case where a tumor antigen or a Th cell specific to the tumor antigen are separately administered to a patient.

A Th cell specific to the tumor antigen as a partial polypeptide of MAGE-A4 may be Th0 cell, Th1 cell or Th2 cell as long as it is a Th cell that produces cytokines by specific stimulation by the tumor antigen, but more preferably Th1 cell. A Th cell specific to the tumor antigen can be induced and prepared from a CD4-positive T cell by incubating the tumor antigen, an antigen-presenting cell expressing an HLA Class II molecule and the CD4-positive T cell under appropriate conditions.

A CD4-positive T cell useful in the method of this invention can be isolated from blood sample by generally known methods such as a method using MACS (Miltenyi Biotec GmbH). In this invention, a CD4-positive T cell collected from a patient with malignant neoplasm to be treated is preferably used.

An antigen-presenting cell useful in the method of this invention may be a cell expressing an HLA Class II molecule on the surface thereof, e.g., B cell, macrophage and non-proliferative transfectant, in addition to dendritic cell, but this invention is not limited thereto.

A tumor antigen as a partial polypeptide of MAGE-A4, an antigen-presenting cell and a CD4-positive T cell may be concurrently incubated, or the tumor antigen and the antigen-presenting cell may be firstly incubated, followed by the CD4-positive T cell in their coexisting state. In incubation, a desired antigen may be presented to the antigen-presenting cell via an HLA Class II molecule in the presence of IL-2 according to known methods for inducing a mature Th cell specific to the antigen from a CD4-positive T cell described, e.g., in a paper of Tim et al. (Immunology Today, Vol. 17, No. 3, pp. 138-146, 1996). Also, based on the descriptions by Nishimura et al. (J. Exp. Med., Vol. 190, No. 5, pp. 617-627, 1999), Th0 cell, Th1 cell or Th2 cell can be specifically induced from a CD4-positive T cell by changing incubation conditions. Such induction can be confirmed by detecting cytokines in each cell produced when such a cell is re-stimulated by the tumor antigen as a partial polypeptide of MAGE-A4 (see the above description by Tim et al., etc.). Cytokine production can be confirmed, using ELISA method and other various methods.

An embodiment of a polypeptide of this invention is an antigenic polypeptide corresponding to an amino acid sequence of No. 259 to 278 of a tumor antigen protein (the above Non-Patent Document 5) known as MAGE-A4 (SEQ ID No: 1, hereinafter called M38) and an amino acid sequence of No. 280 to 299 of MAGE-A4 (SEQ ID No: 2, hereinafter called M41).

In connection with amino acid sequences of polypeptides of M38 (SEQ ID No: 1) and M41 (SEQ ID No: 2), a polypeptide comprising an amino acid sequence having the following characteristic b), c), d), e) or f) can be used as a tumor antigen of this invention.

b) An amino acid sequence, wherein one to several tens of any amino acids are added to N terminus and/or C terminus of an amino acid sequence represented by SEQ ID No: 1 or No: 2;

c) An amino acid sequence, wherein one to five amino acids from N terminus and/or C terminus of an amino acid sequence represented by SEQ ID No: 1 or No: 2 are deleted;

d) An amino acid sequence, wherein one to several amino acid residues of an amino acid sequence represented by SEQ ID No: 1 or No: 2 are substituted and/or deleted;

e) An amino acid sequence, wherein one to several tens of any amino acids are added to N terminus and/or C terminus of an amino acid sequence, wherein one to several amino acid residues of an amino acid sequence represented by SEQ ID No: 1 or No: 2 are substituted and/or deleted; and f) An amino acid sequence, wherein one to several amino acid residues are substituted in an amino acid sequence, wherein one to five amino acids from N terminus and/or C terminus of an amino acid sequence represented by SEQ ID No: 1 or No: 2 are deleted.

By definition, an amino acid sequence having the above characteristic b), c), d), e) or f) comprises a polypeptide that retains an epitope on M38 or M41 and has a cytokine-producing activity in an A4/Th cell, or has an epitope that induces a Th cell specific to MAGE-A4, M38 and/or M41 from a CD4-positive T cell.

A type of amino acid residue that is substituted, deleted or added defined by the above characteristic b), c), d), e) or f) is not particularly limited within a range where the above-described activity and function of an polypeptide are maintained, but "one to several tens of any amino acids are added" in b) and e) means 1 to 50 amino acids, preferably 1 to 30 amino acids, and more preferably 1 to 15 amino acids.

M38 and M41 have a cytokine-producing activity in an A4/Th cell induced from a CD4-positive T cell by incubating MAGE-A4, an antigen-presenting cell and a CD4-positive T cell. Specifically, M38 and M41 have an epitope recognized by the A4/Th cell, which is presented by an MHC Class II molecule expressing on the surface of an antigen-presenting cell that endocytoses MAGE-A4. Thus, a treating agent for malignant neoplasm containing MAGE-A4, M38 and/or M41 and an A4/Th cell is an embodiment of this invention. Another embodiment of this invention is a treating agent for malignant neoplasm containing a Th cell specific to M38 and/or M41 induced from a CD4-positive T cell by incubating MAGE-A4, M38 and/or M41, an antigen-presenting cell and the CD4-positive T cell.

M38 and M41 are polypeptides identified as a tumor antigen in a human whose HLA genotypes are HLA-DRB1*0101 and HLA-DRB1*1405 and in a human whose HLA genotypes are HLA-DRB1*0201 and HLA-DRB1*0501, respectively. Therefore, it is believed that M38 and a polypeptide comprising an amino acid sequence in the above characteristic b), c), d), e) or f) based thereon are particularly effective in a human whose HLA genotype is HLA-DRB1, and more specifically HLA-DRB1*0101. Meanwhile, M41 and a polypeptide comprising an amino acid sequence in the above characteristic b), c), d), e) or f) based thereon are particularly effective in a human whose HLA genotype is HLA-DPB1, and more specifically HLA-DPB1*0501.

Each of the above-described polypeptides is a new polypeptide useful as an ingredient of a treating agent for malignant neoplasm, having an activity of inducing a Th cell specific to the polypeptide from a CD4-positive T cell and/or a cytokine-producing activity in a Th cell or an A4/Th cell. A cytokine-producing activity in a Th cell specific to each of the above-described polypeptides or MAGE-A4 can be confirmed by measuring a volume of a cytokine produced by stimulating the Th cell by the polypeptide, using various known methods. For example, a volume of interferon gamma (INF-γ) produced can be readily measured and confirmed, using commercially available ELISA kits like the one of BD Bioscience.

An embodiment of this invention defines each of said polypeptides, to which His-Tag widely used as a tag sequence useful in e.g. separation and refinement of proteins, an appropriate linker sequence and an amino acid sequence of a marker protein like GFP can be added, as well as labeled compounds such as biotin, as long as such a polypeptide has a specific constituent amino acid sequence. Thus, this invention essentially includes even a polypeptide comprising an amino acid sequence to which any amino acid residue is added for use in, other than the production of cytokines in a Th cell and an A4/Th cell specific to the polypeptide or the induction of said cell from a CD4-positive T cell in an amino acid sequence comprising a polypeptide as an embodiment of this invention, or a polypeptide in which an appropriate labeled compound is added to the polypeptide of this invention, as long as they have a cytokine-producing activity in the cell or an epitope that induces the Th cell specific to the polypeptide from the CD4-positive T cell.

A polypeptide of this invention can be produced as a recombinant protein by applying various known gene recombination methods to DNA encoding the polypeptide. Specifically, the process consists of synthesizing DNA encoding the polypeptide of this invention using an appropriate DNA synthesizer, constructing an expression vector expressing the polypeptide of this invention by appropriately selecting or combining various methods described in reference books in the technical field such as Sambrook et al. Molecular Cloning: A Laboratory Manual, 2nd edition (Cold Spring Harbor Laboratory Press, 1989) and transforming an appropriate host cell like coli bacillus using this expression vector to produce the polypeptide. As described above, various operations used in the production of a recombinant polypeptide can be additionally introduced, like the addition of His-tag.

A polypeptide of this invention can be chemosynthetically produced using an amino acid modified by various protecting groups as a raw material. Methods for organochemically synthesizing a polypeptide without using a gene or a host cell are well known to those skilled in the art. For example, "Jikken Kagaku Koza (Courses in Experimental Chemistry) 16, 5th edition, Yukikagobutsu-no-Gosei (Synthesis of Organic Compounds) IV" (Saburo Aimoto et al., The Chemical Society of Japan) describes various polypeptide chemical synthesis methods, by any of which the polypeptide of this invention can be synthesized. Also, the polypeptide can be synthesized using a commercially available apparatus known as peptide synthesizer.

The above polypeptide can induce a CD-positive 4T cell to a Th cell by incubating the polypeptide, an antigen-presenting cell and a CD-positive 4T cell under appropriate conditions. Thus, this invention also provides a method for inducing a Th cell specific to the above polypeptide and/or MAGE-A4 by incubating in vitro an antigen-presenting cell expressing an HLA Class II molecule, a CD-positive 4T cell and the above polypeptide. In incubation, one or more substances of IFN-γ, IL-12 and anti-IL-4 antibody are preferably added to an incubator, as well as IL-2. Under this incubation condition, a Th1 cell can be induced so as to produce IFN-γ and provide a low IL-4 producing ability.

An antigen-presenting cell useful in this method can be available as long as it expresses an HLA Class II molecule on the surface thereof, such as B cell, macrophage, monocyte and non-proliferative transfectant, in addition to dendritic cell, but this invention is not limited thereto. The above polypeptide may be incubated with an antigen-presenting cell and a CD4-positive T cell. The polypeptide of this invention and an antigen-presenting cell may be firstly incubated, followed by a CD4-positive T cell in their coexisting state. The incubation of the polypeptide of this invention, an antigen-presenting cell expressing an HLA Class II molecule on the surface thereof and a CD4-positive T cell is defined, as described above, according to a known method for presenting a desired antigen to the antigen-presenting cell via an HLA Class II molecule and inducing a mature Th cell specific to the antigen from a CD4-positive T cell, e.g., the above method of Tim et al.

According to the method of this invention, an antigen-presenting cell and a CD4-positive T cell are collected from a patient to be incubated with the polypeptide of this invention, resulting in in vitro induction and cultivation of an A4/Th cell. By returning the A4/Th cell induced by this method to the patient, the immune system thereof can be activated, leading to regression of a tumor cell and thus treatment of malignant neoplasm. By administering the A4/Th cell induced by this method or the A4/Th cell induced using MAGE-A4 and the polypeptide of this invention to the patient, malignant neoplasm can be treated.

A polypeptide of this invention can induce an antibody that can specifically recognize MAGE-A4 in appropriate animals like a rabbit by administrating the polypeptide thereto. This type of antibody can specifically detect a cell expressed by MAGE-A4 or cancer cell, thereby providing an efficient diagnosis of malignant neoplasm.

Moreover, a polypeptide of this invention can be used in a method for confirming the state of an immunocyte that attacks a tumor cell in vivo expressing MAGE-A4 in a patient and a method for monitoring the induction of an immunocyte that attacks a tumor cell expressing MAGE-A4 by administering a treating agent for malignant neoplasm of this invention or a vaccine to a patient, respectively.

A treating agent of this invention may contain a tumor antigen and a Th cell specific thereto, and as long as actions thereof are not inhibited, various excipients generally used in medicine formulation and other pharmaceutically active ingredients, etc. Particularly, the treating agent for malignant neoplasm of this invention is preferably used as a buffer liquid or a liquid medium that can stably retain a tumor antigen and a Th cell specific thereto. Non-limiting examples of buffer solution include a neutral pharmacologically permissible buffered physiological saline or a phosphate buffered saline. The buffer solution may further contain carbohydrates like glucose, mannose, sucrose, dextran and mannitol, proteins, amino acids, antioxidants, bacteriostatic agent, chelating agent (e.g. EDTA or glutathione), adjuvant (e.g. aluminum hydroxide), tonicity adjusting agent, suspension, thickening agent and/or preservative, etc. The treating agent for malignant neoplasm of this invention is preferably used as a mixture of a tumor antigen and a Th cell specific thereto, but a tumor antigen and a Th cell specific thereto may be separately preserved and mixed to be administered to a patient as a kit in use.

The present invention will be described in detail in each of the following examples, but this invention is not particularly limited thereto.

EXAMPLE

Example 1

Identification of M38

1) Preparation of Recombinant MAGE-A4

After an RNA was extracted from an operatively extracted tumor using ISOGEN(NIPPON GENE), the RNA was subjected to amplification reaction with primers of A4F (ggatccatgtcttctgagcagaagag, SEQ ID No: 5) and A4R (aagctttcagactccctcttcctcctcctctaa, SEQ ID No: 6) using SuperScriptII one-step RT-PCR system (Invitrogen) to obtain a cDNA encoding MAGE-A4 (SEQ ID No: 4). The amplified product was cloned using TOPO TA cloning kit (Invitrogen) and a base sequence of a cDNA portion of MAGE-A4 was confirmed by comparing with GenBank Nm_001011550. Afterward, a gene fragment was prepared using restriction enzymes of BamHI and HindIII, which was then incorporated into a commercially available ring-opened expression vector plasmid pQE9 (QIAGEN) to prepare an expression vector pQE9-MAGEA4 that can express MAGE-A4.

Using the expression vector pQE9-MAGEA4, a recombinant cell obtained by transforming an *Escherichia coli* BL-21 (DE3) codon plus (Stratagene) was cultured in an LB medium so that OD=1.0. Then, IPTG (SIGMA) was added thereto to induce the expression so as to set its final concentration at 1 mM, and the product was cultured at 37° C. for 4 hours. Thereafter, a microbial body was collected by centrifugal separation at a speed of 6000 rpm for 15 minutes. After the microbial body was suspended in 10 ml of 10 mM Tris-HCl buffer solution containing 300 mM NaCl and 20 mM imidazol, it was subjected to ultrasonic fragmentation. After supernatants in fragmented microbial cell solution were collected by centrifugal separation at a speed of 15000 rpm for 15 minutes, they were passed through a 0.45 cm filter (Sartorius) and eluted by pH-gradient method (pH ranging from 8.0 to 4.5), using an equilibrated Ni Sepharose HP (Amersham Biosciences). Subsequently, a fraction containing MAGE-A4 was confirmed by SDS-PAGE using 15% acrylamide gel and collected. MAGE-A4 contained in the collected fraction was subjected to centrifugal concentration using Amicon Ultra 10000 cut (MILLIPORE), and a buffer solution was replaced with PBS to obtain a recombinant MAGE-A4 used in the following tests.

2) Preparation of Monocyte-Derived Dendritic Cell (mDC)

A peripheral blood mononuclear cell (PBMC) was separated from peripheral blood of a healthy individual whose HLA genotype is HAL-DRB1*0101 and HLA-DRB1*1405, using Ficoll-Paque PLUS (GE Healthcare) overlay technique. After PBMC was cultured in serum-free AIM-V medium (Invitrogen) in a 5% $CO_2$ incubator at 37° C. for 2 hours, a nonadherent cell was removed therefrom by medium exchange. An adherent cell was cultured in a serum-free AIM-V medium containing 30 ng/ml GM-CSF and 30 ng/ml IL-3 (both purchased from PeproTech EC Ltd., London, England) and a culture solution was replaced with a new one having the same compositions 3 and 5 days later. 7 days after the culturing started, the culture was digested with 2.5 mg/ml trypsin (Sigma) and the adherent cell was separated from the incubator by pipetting and collected to obtain mDC as an antigen-presenting cell (APC). Using MACS (purchased from Miltenyi Biotech), an anti-CD4 antibody adsorbent cell was isolated from the nonadherent cell obtained in mDC induction to obtain a CD4-positive T cell.

3) Establishment of Th Cell Specific to MAGE-A4 Using Recombinant MAGE-A4

After the recombinant MAGE-A4 was added to an mL medium containing $1 \times 10^6$ mDCs prepared in 2) so as to set its final concentration at 50 µg/ml and the product was cultured in 5% $CO_2$ incubator at 37° C. for 2 hours, mitomycin (MMC, Kyowa Hakko Kirin Co., Ltd.) was added thereto and incubated for 45 minutes to perform antigen-presenting treatment. CD4-positive T cells ($1 \times 10^6$/well) and antigen presentation-treated mDCs ($1 \times 10^5$/well) were added to one well of a 24-well plate (BD Bioscience, CA) and the product was subjected to cocultivation in 1000 µL of a culture solution. The culture solution was an AIM-V medium containing 5% AB serum from healthy volunteer individuals. 7 days after cocultivation started, mDCs antigen-presentation-treated in another well as above ($1 \times 0^5$/well) were prepared and CD4-positive T cells cocultivated for 7 days were moved thereto for re-stimulation. 2 days later, a recombinant IL-2 was added thereto so as to set its final concentration at 10 U/mL and cultivated in a 5% $CO_2$ incubator for 7 days to establish an A4/Th cell.

4) Peptide Synthesis

Like a peptide comprising an amino acid sequence of No. 1 to 20 of MAGE-A4, a peptide comprising an amino acid sequence of No. 7 to 27 of MAGE-A4 and a peptide comprising an amino acid sequence of No. 13 to 34 of MAGE-A4, all 44 peptides (M1 to M44) from N terminus to C terminus of MAGE-A4, comprising 20 amino acid residues having an overlapping sequence consisting of 7 amino acids at C terminus and/or N terminus were designed and each chemically synthesized. Moreover, 8 types of mixed peptides, each composed of 5 peptides grouped from M1 to M40 (defined as MIX1 to MIX8), and one mixed peptide composed of 4 peptides from M41 to M44 (defined as MIX9) were prepared.

5) Identification of Polypeptide

The A4/Th cell prepared in 3) was divided equally into 9 portions, to which MIX1 to MIX9 mixed peptides prepared in 4) were each added so as to set its final concentration at 10 µg/mL and the product was re-stimulated by cocultivating with MMC-treated PBMC. One week after the re-stimulation, the operation of placing each cell in a new medium, containing a mixed peptide whose concentration is identical to the cell, was repeated 3 to 4 times. 14 or more days after the re-stimulation started, the culturing was continued with a final concentration of IL-2 at 20 U/mL. Thereafter, a volume of IFN-γ contained in culture supernatants was measured using ELISA kit (BD Bioscience, CA).

Figure 2:
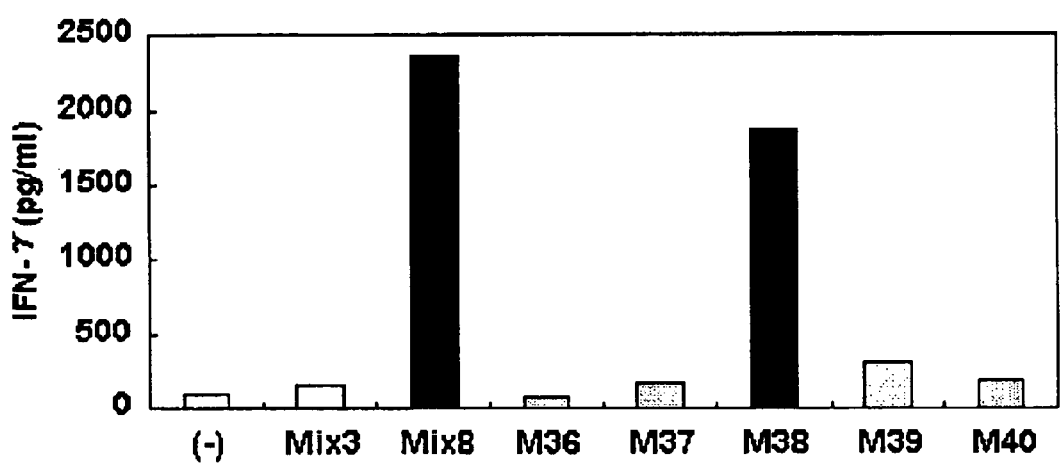
FIG. 2 is a graph indicative of volumes of INF-γ produced by an A4/Th cell induced from a human whose HLA genotype is HLA-DRB1 by adding polypeptides M36 to M40 to the A4/Th cell, respectively.

Consequently, IFN-γ production was found in an A4/Th cell re-stimulated by a mixed peptide MIX8 (FIG. 1). Moreover, to identify a polypeptide having an epitope presented by an HLA Class II molecule in 5 types of polypeptides (M36 to M40) contained in MIX8, PBMC was stimulated using each of the peptides M36 to M40 contained in MIX8 individually to measure IFN-γ contained in culture supernatants using ELISA kit (BD Bioscience, CA). As a result, it was found that re-stimulation by M38 promotes IFN-γ production by an A4/Th cell (FIG. 2) and M38 is a polypeptide having an epitope presented by an HLA Class II molecule whose genotype is HLA-DRB1.

Example 2

Identification of M41

Figure 3:
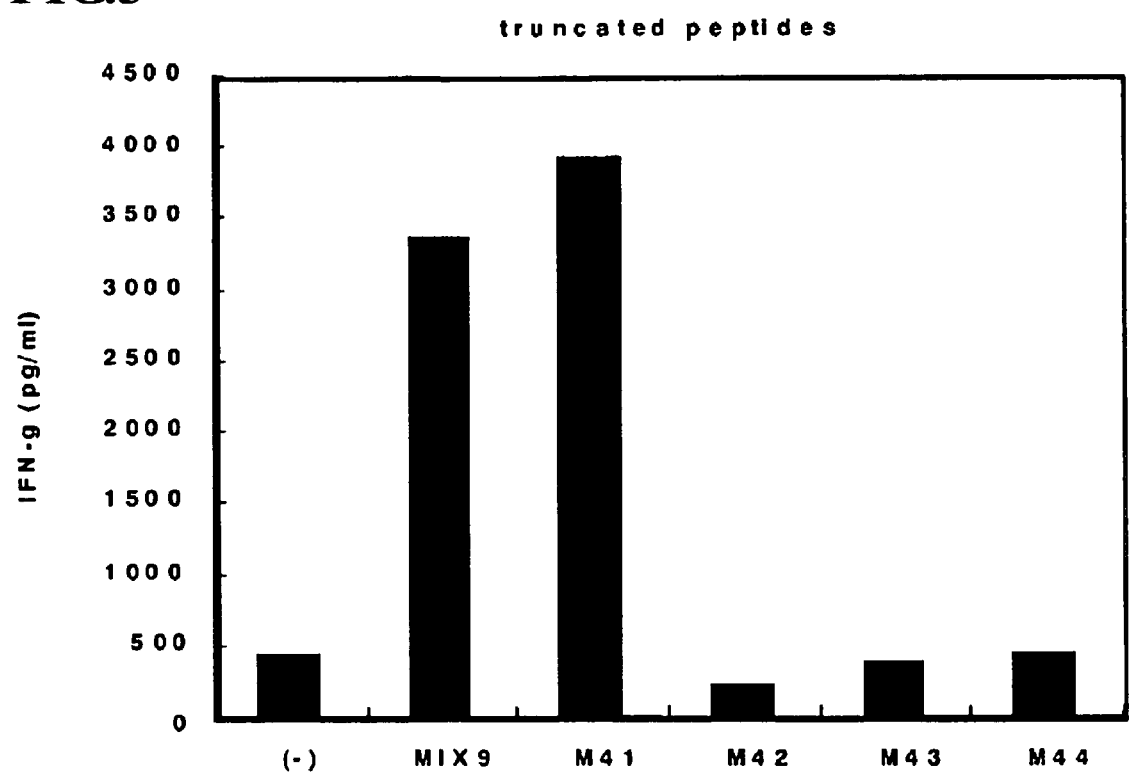
FIG. 3 is a graph indicative of volumes of INF-γ produced by an A4/Th cell induced from a human whose HLA genotype is HLA-DRB1 by adding a mixed peptide MIX9 and polypeptides M41 to M44 to the A4/Th cell, respectively.

Here, the process was identical to 1) to 5) of Example 1, other than the separation of PBMC from peripheral blood of a healthy individual whose HLA genotype is HLA-DPB1*0210 and HLA-DPB1*0510 using Ficoll-Paque PLUS (GE Healthcare) overlay technique and use of a different peptide MIX selected. It was found that M41 is a polypeptide having an epitope presented by an HLA Class II molecule whose genotype is HLA-DPB1. (FIG. 3)

Example 3

Induction of A4/Th1 Cell by M38 and M41

After M38 or M41 was added to an mL medium containing $1.5 \times 10^5$ mDCs prepared in 2) of Example 1 so as to set its final concentration at 10 µg/ml and the product was cultured in 5% $CO_2$ incubator at 37° C. for 2 hours, mitomycin (MMC, Kyowa Hakko Kirin Co., Ltd.) was added thereto and incubated for 45 minutes to perform antigen-presenting treatment. CD4-positive T cells ($1 \times 10^6$/well) were added to one well of a 24-well plate (BD Bioscience, CA), and IL-12 (100 IU/mL, Genetics Institute) and anti-IL-4 antibody (5 µg/mL, BD Pharmingen) were added to antigen-presented mDCs ($1 \times 10^5$/well), which were subjected to cocultivation in 1000

μL of culture solution. The culture solution was an AIM-V medium containing 5% AB serum from healthy volunteer individuals. 7 days after cocultivation started, mDCs antigen-presentation-treated in another well as above (1×10⁵/well) were prepared and CD4-positive T cells cocultivated for 7 days were moved thereto for re-stimulation. 2 days later, a recombinant IL-2 was added thereto so as to set its final concentration at 10 U/mL and cultivated in a 5% $CO_2$ incubator for 7 days to obtain a Th1 cell from M38 and M41, respectively.

Figure 4A:
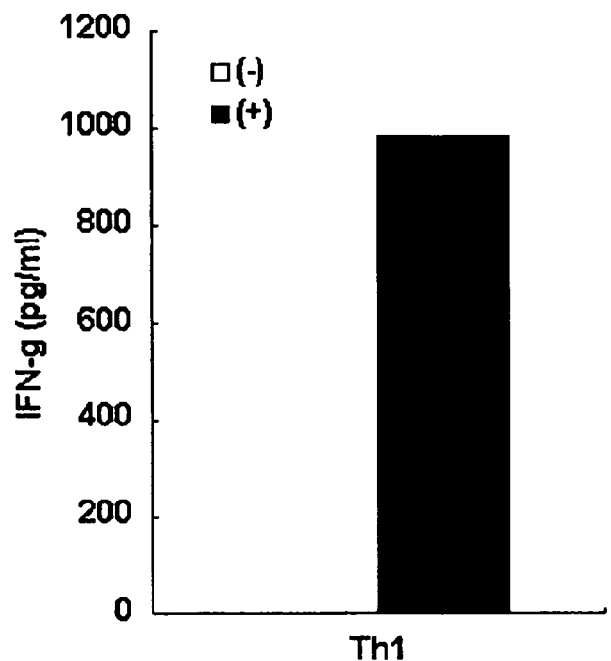
FIG. 4a is a graph indicative of volumes of INF-γ produced by an M38/Th1 cell induced by a method described in Example 3 by adding M38 to the M38/Th1 cell.
Figure 4B:
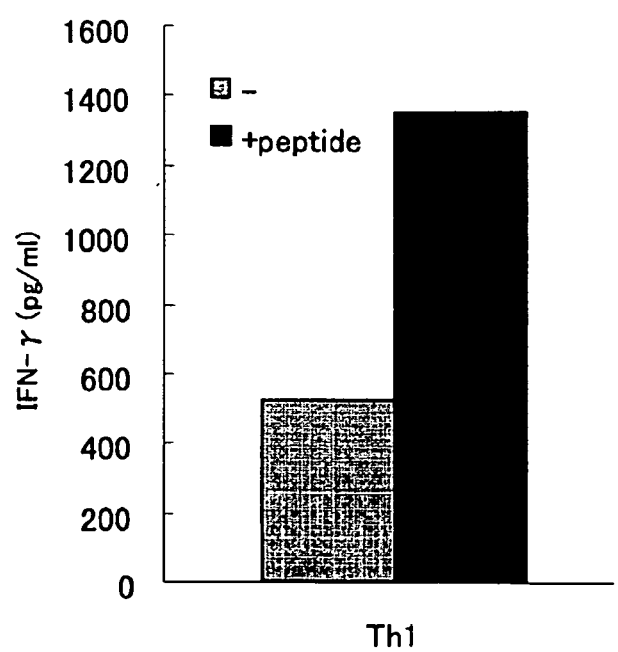
FIG. 4b is a graph indicative of volumes of INF-γ produced by an M41/Th1 cell induced by a method described in Example 3 by adding M41 to the M41/Th1 cell.

When 50 μg/mL of a recombinant MAGE-A4 prepared in 1) of Example 1 was added to an M38/Th1 cell and an M41/Th1 cell, respectively, IFN-γ production was confirmed in both types of cells. When 10 to 20 μg/mL of M38 and M41 were added to an M38/Th1 cell and an M41/Th1 cell, respectively in lieu of a recombinant MAGE-A4, IFN-γ production was confirmed as in the case where the recombinant MAGE-A4 was added. (FIGS. 4a and 4b)

Example 4

Production of Cytokines from A4/Th Cell by M41

Figure 5A:
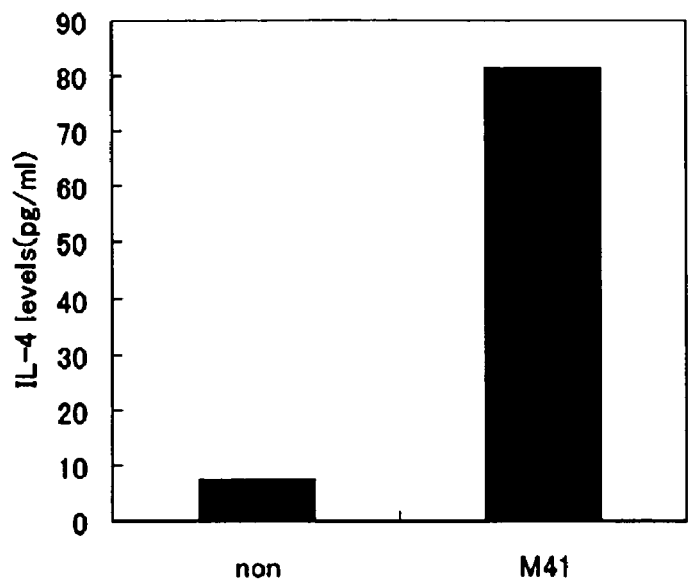
FIG. 5a is a graph indicative of volumes of IL-4 produced by an A4/Th1 cell induced by a method described in Example 4 by adding M41 to the A4/Th1 cell.
Figure 5B:
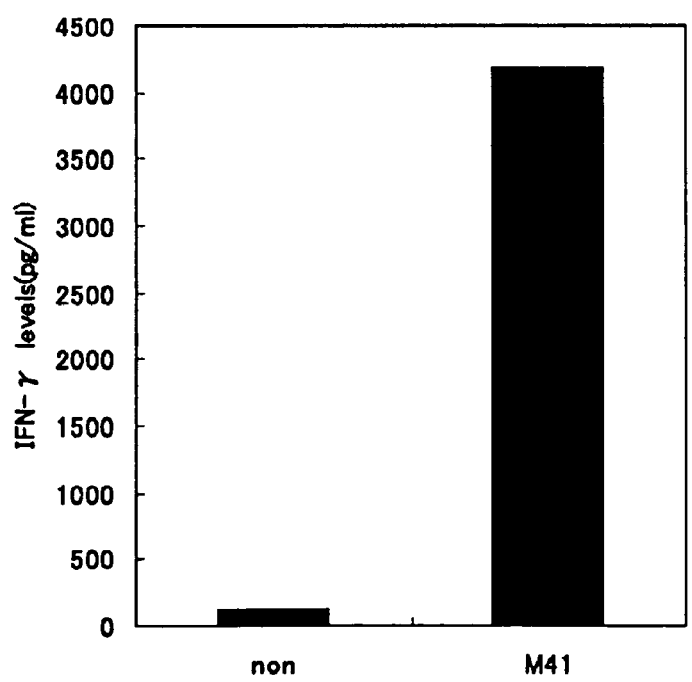
FIG. 5b is a graph indicative of volumes of INF-γ produced by an A4/Th1 cell induced by a method described in Example 4 by adding M41 to the A4/Th1 cell.

Using the method in Example 2, when 10 μg/mL of M41 was experimentally added to an A4/Th in lieu of a recombinant MAGE-A4 protein, IL-4 and IFN-γ production was confirmed. (FIGS. 5a and 5b)

Example 5

1) From a healthy individual whose HLA genotype is HLA-DPB1*1403, PBMC and an A4/Th cell having the same genotype HLA-DPB1*1403 were prepared according to the methods described in 2) and 3) of Example 1.

2) A PBMC having an HLA genotype of HLA-DPB1*1403 and a PBMC whose HLA genotype is HLA-DPB1*0201 and HLA-DPB1*0501 prepared in Example 2 were cultured in culture supernatants of 50% EB virus-producing cell B95-8 (from JCRB CELL BANK) and RPMI medium (Sigma) containing 10% Fetal Calf Serum (FCS) and cyclosporin A, respectively in 5% $CO_2$ at 37° C. for 10 days. After the culturing, the cells were washed and added to a fresh RPMI medium containing 10% FCS. Then, cells that proliferated on the medium were collected to prepare 2 types of EB virus lymphoblastoid cell line (LCL) with different genotypes.

Figure 6:
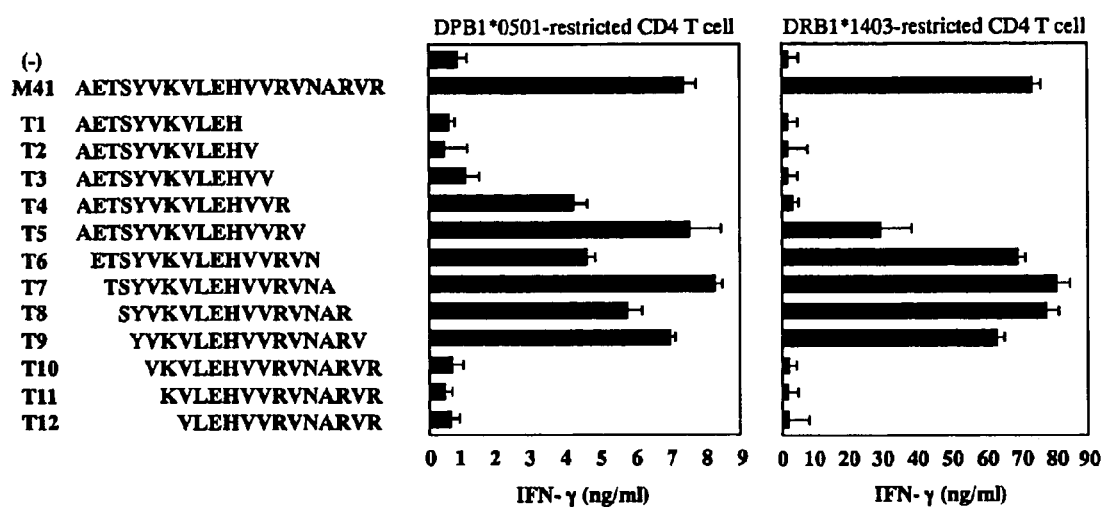
FIG. 6 is a graph indicative of amino acid sequences of M41 variants T1 to T12 (SEQ ID No: 7 to 18), in which amino acids are deleted at terminus, and volumes of INF-γ produced by an A4/Th1 cell by adding amino acid-deleted M41 variants to the A4/Th1, respectively.

3) M41 modified polypeptides T1 to T12 (SEQ ID No: 7 to No: 18), comprising an amino acid sequence, in which 5 to 9 amino acid residues are deleted from N terminus and/or C terminus of an amino acid sequence of M41 (SEQ ID No: 2), were chemically synthesized. An RPMI medium containing 10% FCS having 2 types of 2×10⁵ LLC in the above 2) was fed through a 15 mL conical tube to which 10 μg of said peptides were each added to be cultured at 37° C. for 2 hours, thereafter the medium was removed by centrifugal force and washed with PBS. An RPMI medium containing 10% FCS having washed 2×10⁴ cells and an RPMI medium containing 10% FCS having 5×10⁴ A4/Th cells having genotypes corresponding thereto respectively were mixed in a 96-well U-bottom plate. After the mixture was cultured at 37° C. for 20 to 24 hours, culture supernatants were collected and IFN-γ contained therein was measured using ELISA kit (BD Bioscience). FIG. 6 shows the results.

Deletion of amino acids from C terminus to No. 5 of M41 has no impact on IFN-γ production inducing ability, but it was found that deletion of amino acids from C terminus to No. 6 reduces IFN-γ production inducing ability in cases where HLA genotype is DRB1*1403. Also, deletion of amino acids from N terminus to No. 4 of M41 has no impact on IFN-γ production inducing ability, but it was confirmed that deletion of amino acids from N terminus to No. 5 reduces IFN-γ production inducing ability independent of HLA genotype. Thus, deletion of amino acid sequences of this invention is preferably found from N terminus (No. 1) to No. 4, from C terminus (No. 1) to No. 6, and more preferably from C terminus (No. 1) to No. 5.

Example 6

Figure 7:
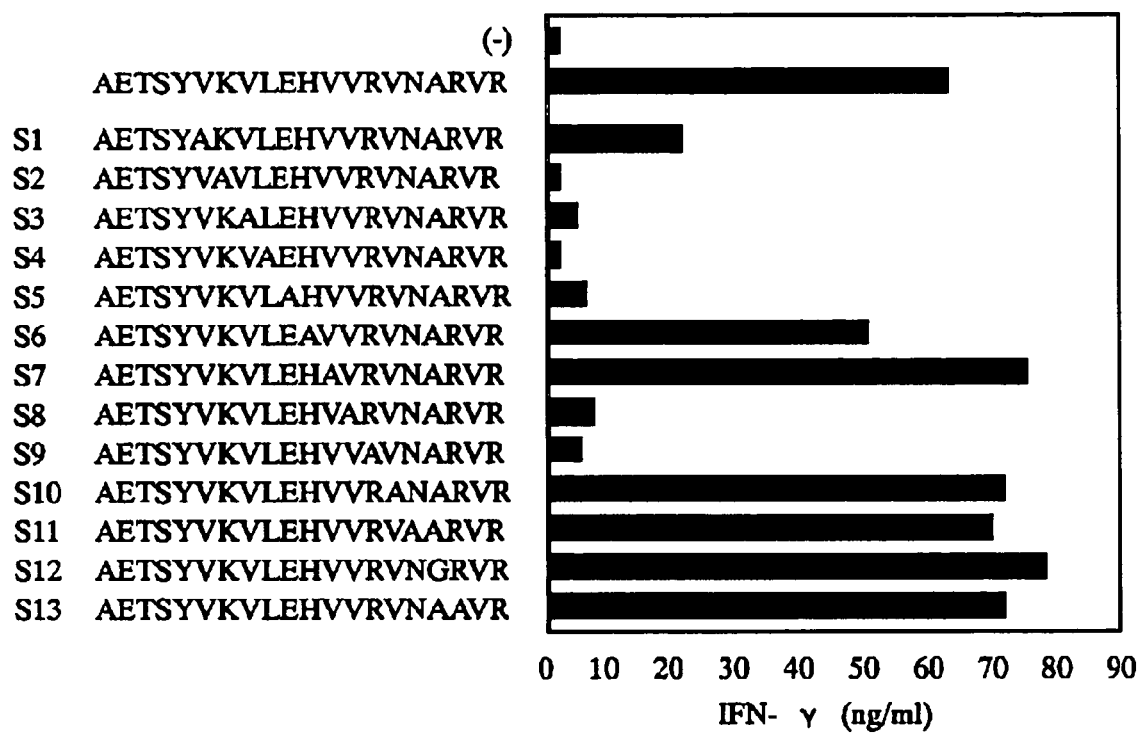
FIG. 7 is a graph indicative of amino acid sequences of M41 variants S1 to S13 (SEQ ID No: 19 to 31), in which amino acid residues are substituted, and volumes of INF-γ produced by an A4/Th1 cell by adding amino acid residue-substituted M41 variants to the A4/Th1 cell, respectively.

Polypeptides S1 to S13 (SEQ ID No: 19 to No: 31), comprising an amino acid sequence, in which amino acid residues from No. 6 to 18 from N terminus of M41 amino acid sequence (SEQ ID No: 2) are each replaced with Ala (Gly only for No. 17 Ala), were synthesized. An RPMI medium containing 10% FCS having 2×10⁴ LLC prepared 2) of Example 5 was fed through a 15 mL conical tube to which 10 μg of said peptides were each added to be cultured at 37° C. for 2 hours, thereafter the medium was removed by centrifugal force and washed with PBS. An RPMI medium containing 10% FCS having washed 2×10⁴ cells and 5×10⁴ A4/Th cells prepared in Example 2 (genotypes are HLA-DPB1*0201 and HLA-DPB1*0501) were mixed in a 96-well U-bottom plate. After the mixture was cultured at 37° C. for 20 to 24 hours, culture supernatants were collected and IFN-γ contained therein was measured using ELISA kit (BD Bioscience). FIG. 7 shows the results.

It was confirmed that regarding M41 amino acid sequence, substitution of alanine for amino acid residues from No. 7 to 10 from N terminus and amino acid residues from No. 12 to 13 from N terminus reduces IFN-γ production inducing ability. Also, substitution for amino acid residues after No. 14 from N terminus showed almost no change in IFN-γ production inducing ability. In this case, however, charged amino acids such as Lys, Arg and Glu and amino acids high in hydrophobicity such as Leu and Val were replaced with a small amino acid of Ala. Highly conservable amino acid substitution like mutual substitution of Lys and Arg, substitution of Asp for Glu and substitution of hydrophobic amino acids such as Val, Leu and Ile for each other are expected to have a different impact as opposed to replacement with Ala. Meanwhile, both C and N terminus portions can be subjected to amino acid substitution from the results of Example 5. From these observations, it is estimated that IFN-γ production inducing ability of M41 in an A4/Th cell is associated with types of amino acid residues from No. 5 to 14 from N terminus of M41 and types of amino acid residues from No. 7 to 10 and from No. 12 to 13 from N terminus of M41.

Example 7

Figure 8:
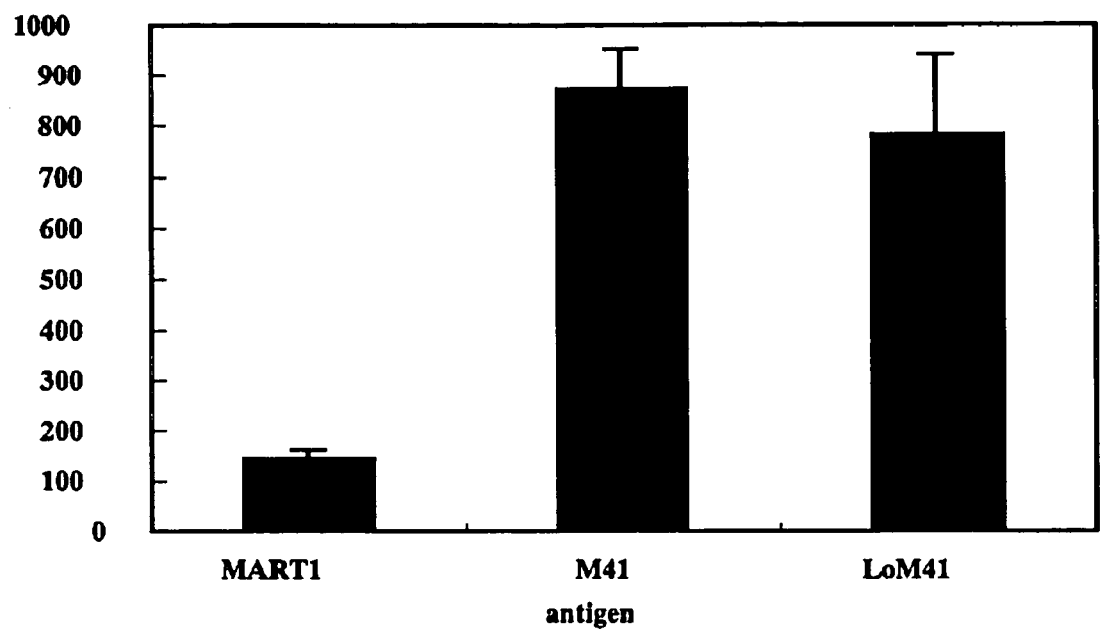
FIG. 8 is a graph indicative of amino acid sequences of variants of M41, to which CTL epitope-presenting amino acid sequences are added, and volumes of INF-γ produced by an A4/Th1 cell by adding the M41 variants to the A4/Th1 cell, respectively.

M41 variants (LoM41), comprising 40 amino acid residues, in which CTL epitope-presenting amino acid sequence (18 amino acid residues) is added to M41, were synthesized. An RPMI medium-containing 10% FCS having 2×10⁴ LLC prepared 2) of Example 5 (genotypes are HLA-DPB1*0201 and HLA-DPB1*0501) was fed through a 15 mL conical tube to which 8 μg of LoM41, M41 and MARTI polypeptide as a control was were each added to be cultured for 2 hours, thereafter the medium was removed by centrifugal force and washed with PBS. An RPMI medium containing 10% FCS having washed 2×10⁴ cells and 5×10⁴ A4/Th cells prepared in Example 2 (genotypes are HLA-DPB1*0201 and HLA-DPB1*0501) were mixed in a 96-well U-bottom plate. After the mixture was cultured at 37° C. for 20 to 24 hours, culture supernatants were collected and IFN-γ contained therein was measured using ELISA kit (BD Bioscience). FIG. 8 shows the results. This test found that LoM41 is a polypeptide whose IFN-γ production inducing ability is equivalent to M41.

Example 8

Figure 9:
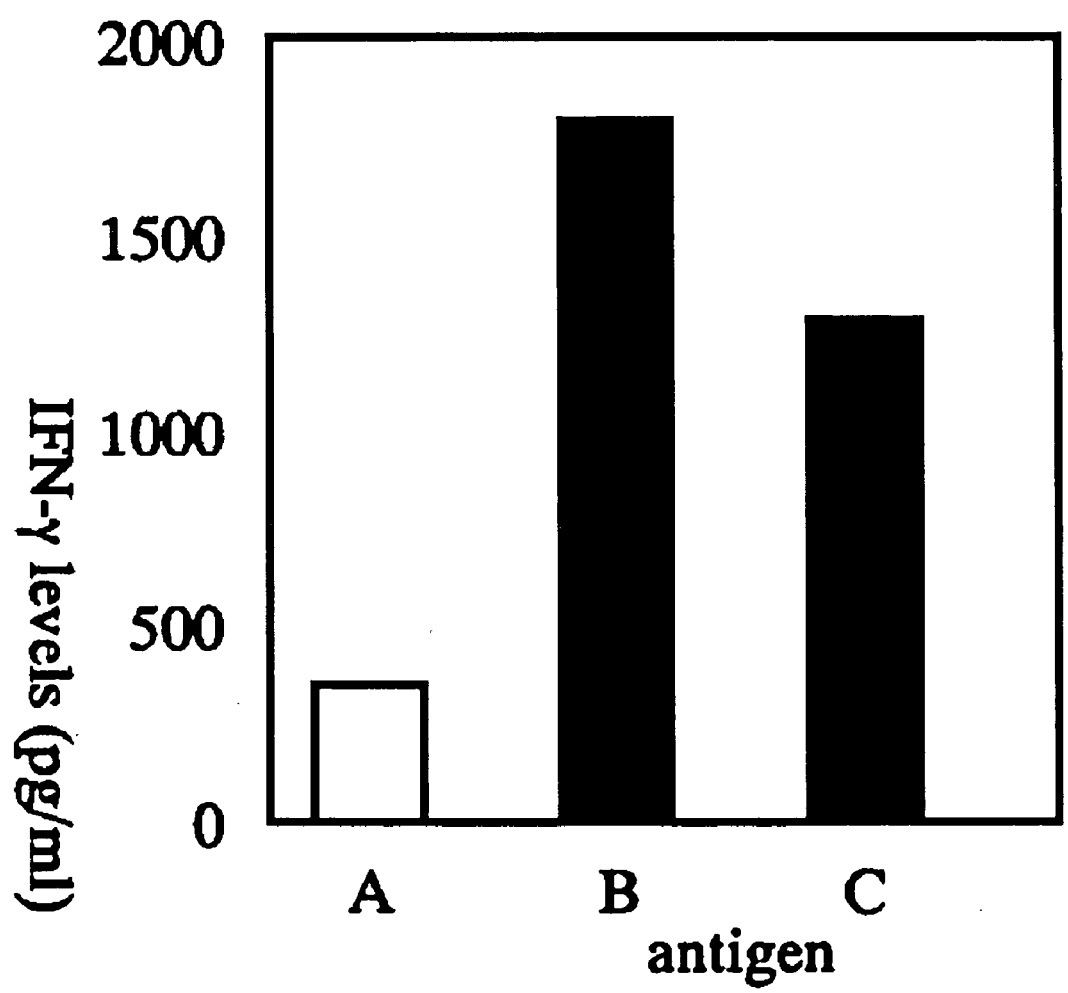
FIG. 9 is graph indicative of the results of a comparative experiment of INF-γ production inducing ability of M38 and recombinant MAGE-A4. (A denotes negative control, B denotes M38 (10 μg/mL) and C denotes recombinant MAGE-A4 (50 μg/mL).)

Using the A4/Th cell prepared in Example 1 and MMC-treated PBMC, IFN-γ production inducing abilities of 1 μg/mL M38 and 50 μg/mL recombinant MAGE-A4 was measured according to a method described in 5) of Example 1. FIG. 9 shows the results. This test found that M38 peptide of this invention has a higher IFN-γ production inducing ability in an A4/Th cell than the recombinant MAGE-A4.

---

The invention claimed is:

1. A polypeptide consisting of an amino acid sequence of SEQ ID No: 2, wherein said polypeptide has cytokine-producing activity in a Th cell specific to MAGE-A4.

2. A polypeptide consisting of an amino acid sequence of SEQ ID No: 2, wherein one to fifty of any amino acids are added to the N terminus and/or the C terminus of an amino acid sequence of SEQ ID No: 2 and the overall length of the polypeptide is from 20 to 120 amino acids and wherein said polypeptide has cytokine-producing activity in a Th cell specific to MAGE-A4.

3. A polypeptide consisting of an amino acid sequence of SEQ ID No: 2, wherein one to five amino acids from the N terminus and/or the C terminus of an amino acid sequence of SEQ ID No: 2 are deleted and the overall length of the polypeptide is no longer than 20 amino acids and wherein said polypeptide has cytokine-producing activity in a Th cell specific to MAGE-A4.

4. The polypeptide as set forth in claim 2 or 3, wherein a polypeptide has an epitope which is from a polypeptide consisting of an amino acid sequence of SEQ ID No: 2 and which induces a Th cell specific to MAGE-A4 from a CD4-positive T cell.

5. An agent for treating malignant neoplasm and inducing a tumor response, consisting of at least one type of the polypeptides as set forth in any one of claim 1, 2 or 3 as an active ingredient.

6. A treating agent for malignant neoplasm consisting of the polypeptide as set forth in any one of claim 1, 2 or 3 and a Th cell specific to the polypeptide or MAGE-A4.

7. An agent for treating malignant neoplasm and inducing a tumor response, consisting of at least one type of the polypeptides as set forth in claim 4 as an active ingredient.

8. A treating agent for malignant neoplasm consisting of the polypeptide as set forth in claim 4 and a Th cell specific to the polypeptide or MAGE-A4.

9. A method for inducing a Th cell specific to MAGE-A4 comprising a process for incubating in vitro at least one type of the polypeptides as set forth in claim 1 or 4, an antigen-presenting cell and a CD4-positive T cell.

* * * * *